United States Patent
Akatsu

(10) Patent No.: US 10,524,938 B2
(45) Date of Patent: Jan. 7, 2020

(54) PRODUCTION METHOD FOR MEDICAL LINEAR MEMBER

(71) Applicant: SYNTEC CORPORATION, Iwaki-shi, Fukushima (JP)

(72) Inventor: Kazumi Akatsu, Fukushima (JP)

(73) Assignee: SYNTEC CORPORATION, Iwaki-Shi (JP)

( * ) Notice: Subject to any disclaimer, the term of this patent is extended or adjusted under 35 U.S.C. 154(b) by 358 days.

(21) Appl. No.: 15/502,660

(22) PCT Filed: Jan. 29, 2016

(86) PCT No.: PCT/JP2016/052717
§ 371 (c)(1),
(2) Date: Feb. 8, 2017

(87) PCT Pub. No.: WO2017/130385
PCT Pub. Date: Aug. 3, 2017

(65) Prior Publication Data
US 2018/0098866 A1    Apr. 12, 2018

(51) Int. Cl.
*A61F 2/82* (2013.01)
*C22F 1/00* (2006.01)
*A61B 17/17* (2006.01)
*A61L 27/50* (2006.01)
*B21F 3/04* (2006.01)
(Continued)

(52) U.S. Cl.
CPC ............ *A61F 2/82* (2013.01); *A61B 17/1789* (2016.11); *A61L 27/50* (2013.01); *B21F 3/04* (2013.01); *C22F 1/006* (2013.01); *A61B 17/8076* (2013.01); *A61F 2002/30996* (2013.01)

(58) Field of Classification Search
None
See application file for complete search history.

(56) References Cited

U.S. PATENT DOCUMENTS

| | | | |
|---|---|---|---|
| 6,264,684 B1 * | 7/2001 | Banas | A61F 2/06 606/195 |
| 2013/0060323 A1 * | 3/2013 | McHugo | A61F 2/90 623/1.18 |
| 2018/0221057 A1 * | 8/2018 | Akatsu | A61B 17/58 |

FOREIGN PATENT DOCUMENTS

| | | |
|---|---|---|
| JP | 2010-232009 | 10/2010 |
| JP | 2011-136143 | 7/2011 |
| JP | 2012-232027 | 11/2012 |

OTHER PUBLICATIONS

International Search Report dated Mar. 1, 2016.

* cited by examiner

*Primary Examiner* — George Wyszomierski
(74) *Attorney, Agent, or Firm* — Rankin, Hill & Clark LLP

(57) ABSTRACT

A production method for a medical linear member is provided which is not abraded upon production and which includes a flat shape in a cross section.

The method includes the steps of: forming a first spiral body (1) of an oval shape in a horizontal section by spirally winding a base body (3), in which a plurality of wires (2) formed of a shape-memory alloy is arrayed, around a winding core (4); subjecting the first spiral body (1) to first shape-memory treatment; cutting the first spiral body (1) into a first predetermined length; forming a second spiral body (5) of a flat shape in a horizontal section by compressing the first spiral body (1) in a direction along a short diameter; subjecting the second spiral body (5) to second (Continued)

shape-memory treatment; and removing the winding core (4) from the second spiral body (5).

4 Claims, 5 Drawing Sheets

(51) Int. Cl.
*A61B 17/80* (2006.01)
*A61F 2/30* (2006.01)

PRODUCTION METHOD FOR MEDICAL LINEAR MEMBER

TECHNICAL FIELD

The present invention relates to a production method for a medical linear member.

BACKGROUND ART

A medical linear member formed into a flat shape in horizontal section has conventionally been used in sternotomy surgery for the purpose of closing a sternal bone after the surgery. For example, known as the aforementioned medical linear member formed into the flat shape in the horizontal section is the one which is formed into a flat cord by braiding a plurality of filaments (for example, see Patent Literature 1).

CITATION LIST

Patent Literature

Patent Literature 1: Japanese Patent Application Laid-Open No. 2012-232027

SUMMARY OF INVENTION

Technical Problem

However, since the aforementioned medical linear member formed into the flat cord is formed by braiding the plurality of filaments, an inconvenience arises such that the filaments rub against each other and are likely to be worn away upon production.

It is an object of the present invention to provide a method capable of resolving the aforementioned inconvenience and producing a medical linear member which is not worn away upon production and which has a flat shape in a cross section.

Solution to Problem

To address the object described above, a production method for a medical linear member of the present invention includes a steps of forming a first spiral body of an oval shape in a horizontal section by spirally winding a base body, in which a plurality of wires formed of a shape-memory alloy is arrayed, around a winding core formed of a flat plate with a space provided in an array direction; a step of subjecting the first spiral body to first shape-memory treatment by heating the first spiral body; a step of cutting the first spiral body into a first predetermined length; a step of forming a second spiral body of a flat shape in a horizontal section by compressing the first spiral body, which has been cut into the predetermined length, in a direction along a short diameter of the oval shape; a step of subjecting the second spiral body to second shape-memory treatment by heating the second spiral body; and a step of removing the winding core from the second spiral body subjected to the second shape-memory treatment.

With the production method of the invention, the base body provided as the one in which the plurality of wires formed of a shape-memory alloy is arrayed, is first spirally wound around the winding core with a space provided in an array direction to form the first spiral body. At this point, since the winding core is formed of the flat plate, the first spiral body is formed into the oval shape, in the horizontal section, which has a long diameter in a width direction of the winding core and a short diameter in a thickness direction thereof.

Next, the first spiral body is subjected to the first shape-memory treatment by heating the first spiral body. Through the first shape-memory treatment, a spiral shape having the space in the array direction is stored into the first spiral body.

Next, the first spiral body is cut into the first predetermined length. The first predetermined length is, for example, a length suitable for the compression performed in a later step.

Next, the first spiral body subjected to the first shape-memory treatment is compressed in the direction along the short diameter of the oval shape. As a result, the second spiral body of the flat shape in the horizontal section is formed from the first spiral body.

Next, the second spiral body is subjected to second shape-memory treatment by heating the second spiral body. Through the second shape-memory treatment, a shape that is flat in the horizontal section is stored into the second spiral body, thereby enabling to obtain the medical linear member of the flat shape in the horizontal section.

It is also possible to simultaneously perform the heating for the second shape-memory treatment at the same time of the compression of the first spiral body. However, performing the heating after the compression of the first spiral body to form the second spiral body allows a reduction in stress imposed on the provided medical linear member.

Next, the winding core is removed from the second spiral body subjected to the second shape-memory treatment, thereby enabling to obtain the medical linear member.

According to the production method of the invention, the first spiral body formed of the oval shape in the horizontal section by spirally winding the base body, in which the plurality of wires are arrayed, around the winding core, is compressed to form the second spiral body of the flat shape in the horizontal section, so that blading causes no abrasion, permitting the production of the medical linear member.

Moreover, according to the production method of the invention, the medical linear member provided as described above is preferably further cut into a second predetermined length. The second predetermined length is, for example, a length adopted upon application of the medical linear member to actual medical treatment, thereby enabling easy application of the medical linear member provided through the production method of the invention to medical treatment.

Moreover, according to the production method of the invention, it is preferable that the compression of the first spiral body is performed by arranging the first spiral body, which has been heated through the first shape-memory treatment, on a base in a state in which the first spiral body is kept heated and pressing a compression member from above. Upon the aforementioned operation, the first spiral body cut into the first predetermined length is likely to be deformed since the first spiral body is kept heated, making it easy to perform the compression.

Moreover, with the production method of the invention, it is preferable that the pressing of the compression member is performed by a spring member which biases the compression member in a direction towards the first spiral body. It is also possible to perform the pressing of the compressing member, for example, by hydraulic pressure, but there is a risk of damage on a hydraulic device by heat when the first spiral body is kept heated, while use of the spring member enables the pressing of the compressing member to be performed without causing any damage by heat.

DESCRIPTION OF EMBODIMENTS

Next, an embodiment of the present invention will be described in more detail with reference to the accompanying drawings.

Figure 1:
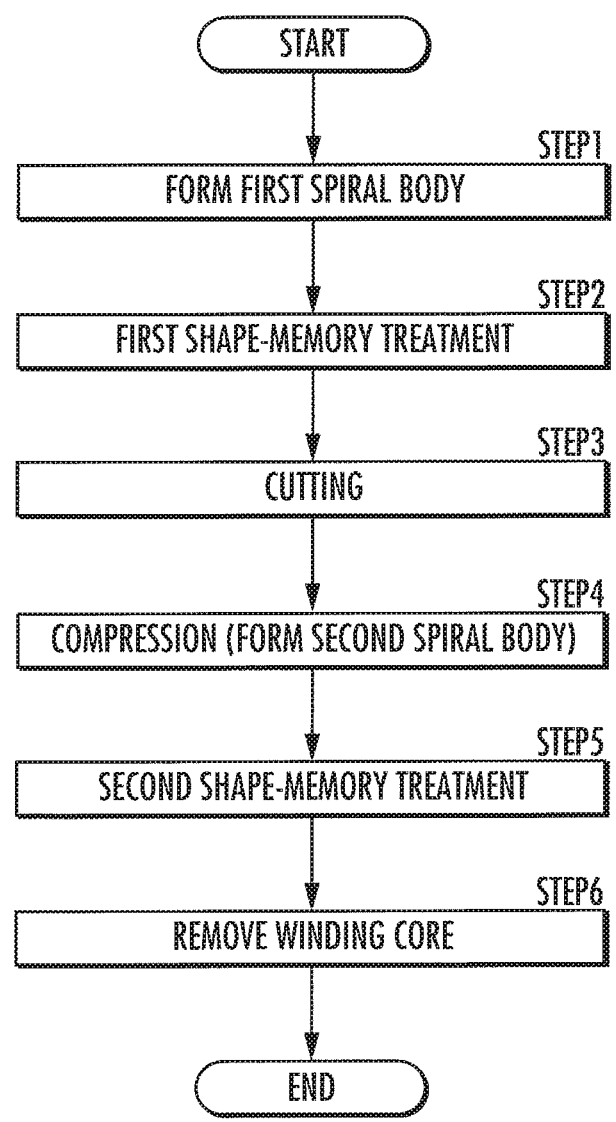
FIG. 1 is a flowchart illustrating production processes for a medical linear member of the present invention.

As illustrated in FIG. 1, with a production method of the present embodiment, a first spiral body 1 is first formed in STEP 1. The formation of the first spiral body 1 is achieved by spirally winding a base body 3, in which a plurality of wires 2 of a shape-memory alloy having a diameter of 0.01 to 5 mm is arrayed in parallel to each other, around a winding core 4 formed of a flat plate having, for example, a width of 0.5 to 100 mm, a thickness of 0.1 to 20 mm, and a length of 3 to 1000 mm with a space S provided in an array direction to thereby provide an oval shape in a horizontal section. The shape in the horizontal section is an oval shape which has a long diameter in a width direction of the winding core 4 and a short diameter in a thickness direction thereof.

Examples of the shape-memory alloy forming the wire 2 include a nickel-titanium alloy and a nickel-titanium-cobalt alloy or the like.

Next, first shape-memory treatment is performed on the first spiral body 1 in STEP 2 of FIG. 1. The first-shape memory treatment is performed by, for example, accommodating the first spiral body 1, with the base body 3 spirally wound around the winding core 4, into a heating furnace, not illustrated, and holding it in a temperature of 150 to 900° C. for 3 to 120 minutes. Since the wire 2 is formed of the shape-memory alloy, performing the aforementioned operation results in storing, into the first spiral body 1, the spirally wound shape with the space S provided in the array direction.

Upon ending of the first shape-memory treatment, the first spiral body 1 is taken out from the heating furnace, cooled, and then cut into a length of 3 to 100 cm, for example, 30 cm in STEP 3 of FIG. 1.

Figure 3:
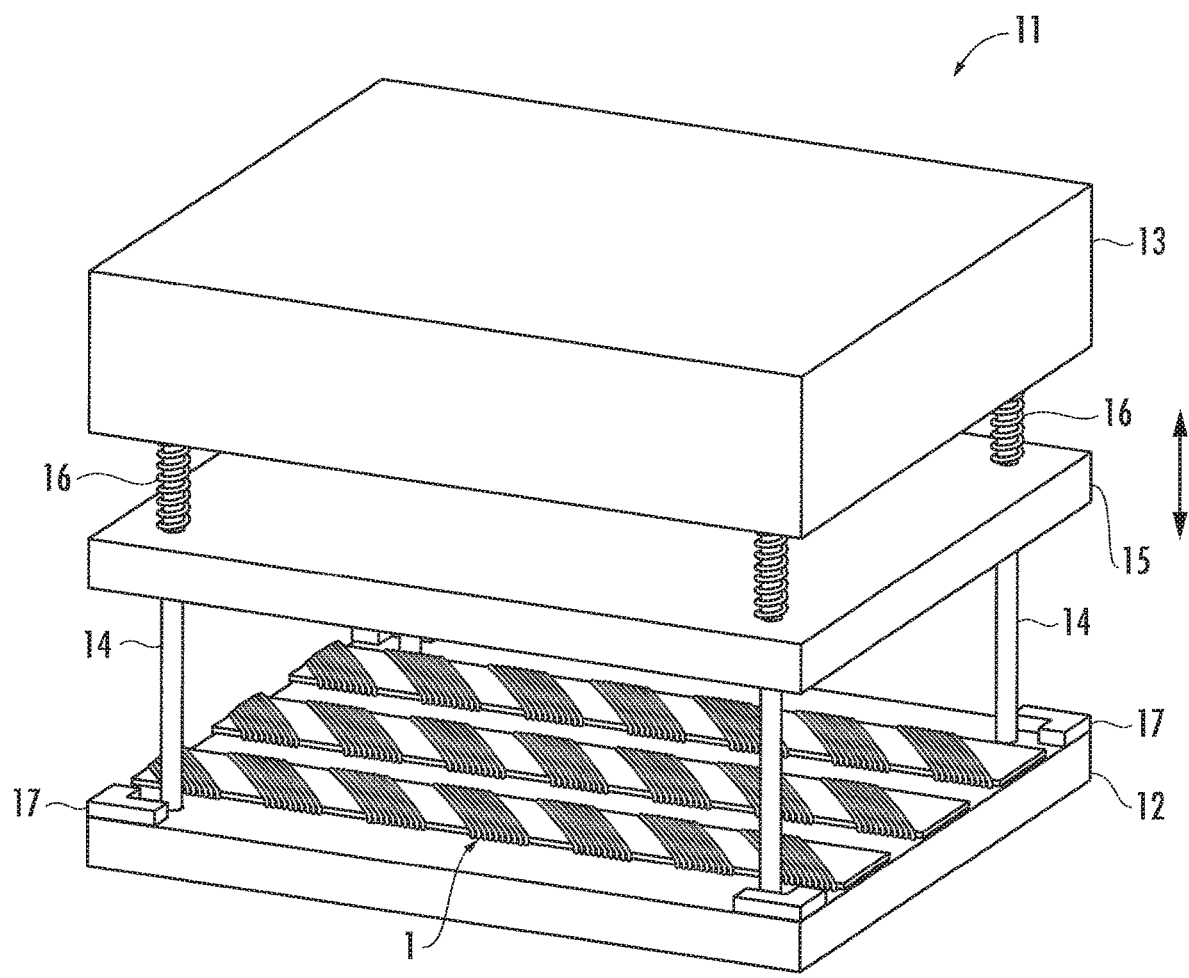
FIG. 3 is a perspective view illustrating configuration of a compression jig which compresses the first spiral body.

Next, the first spiral body 1 is compressed in a direction along the short diameter of the oval shape in STEP 4 of FIG. 1. The compression of the first spiral body 1 is performed by use of a compression jig 11 illustrated in FIG. 3.

The compression jig 11 includes: slide bars 14 provided between a base 12 and a top plate 13; and a press member 15 of a plate-like shape provided in a manner such as to be capable of sliding along the slide bars 14 to move upward and downward. The base 12, the top plate 13, and the press member 15 are each a 30-cm square, in a plan view, which has the slide bars 14 provided at four corners of the square. Moreover, the press member 15 is biased towards the base 12 by spring members 16 disposed on an outer circumference side of the slide bars 14.

Upon the compression of the first spiral body 1 by use of the compression jig 11, in a state in which the press member 15 has been moved towards the top plate 13 against a biasing force of the spring members 16, spacers 17 are arranged at four corners on the base 12. A thickness of the spacer 17 is selected based on a targeted degree of the compression.

Next, the first spiral bodies 1 are loaded onto the base 12. It is possible to load the first spiral bodies 1 onto the base 12, avoiding the spacers 17, with spaces provided therebetween so that the plurality of first spiral bodies 1 are parallel to each other and also do not interfere with each other when compressed. A number of the first spiral bodies 1 loaded onto the base 12 is normally in a range between several bodies and several tens of bodies, depending on a diameter of the first spiral bodies 1.

Figure 4:
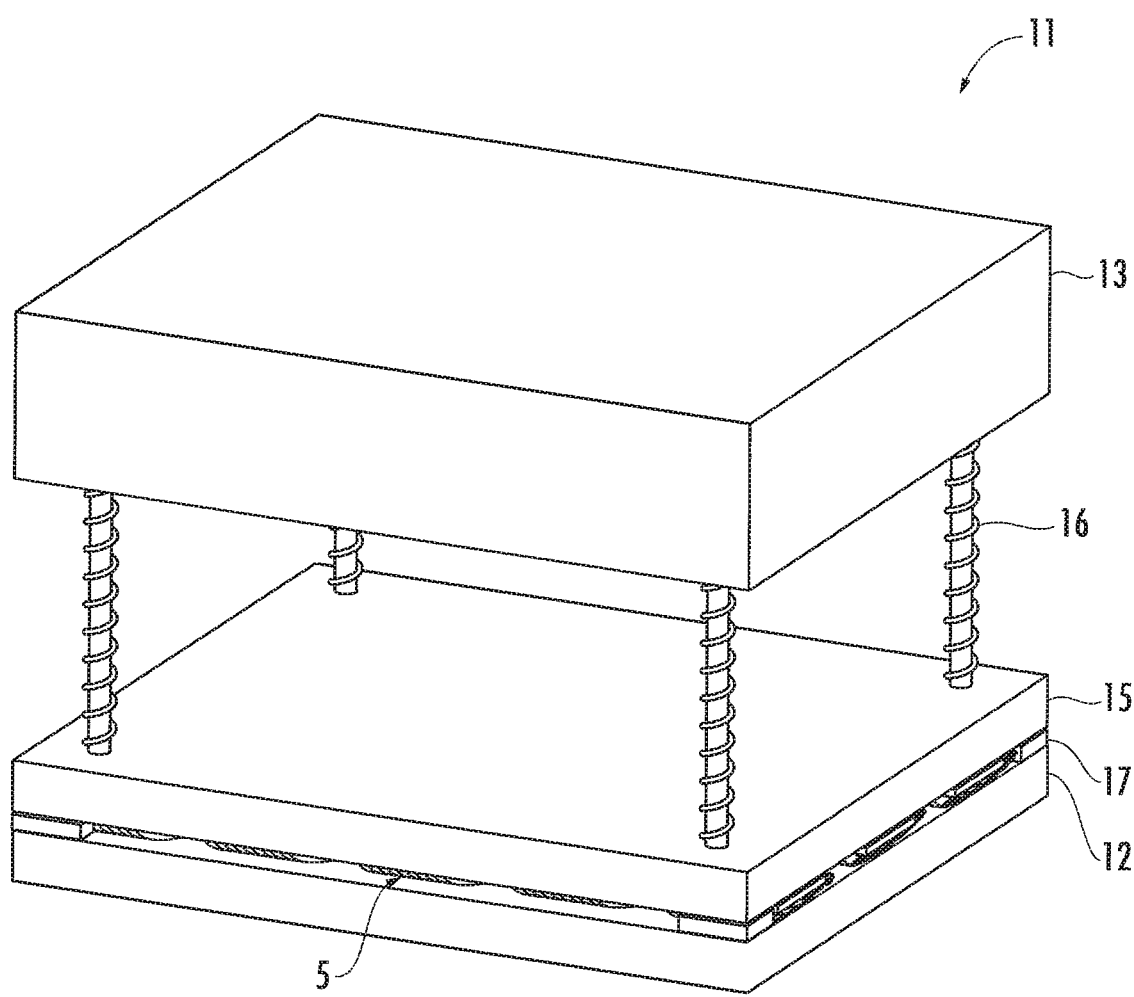
FIG. 4 is a perspective view illustrating a state in which the first spiral body is compressed by the compression jig of FIG. 3.

Next, as illustrated in FIG. 4, the press member 15 moved towards the top plate 13 is pressed by the biasing force of the spring members 16 against the first spiral bodies 1 loaded on the base 12. As a result, the first spiral bodies 1 are compressed in the direction along the short diameter of the oval shape by the press member 15, forming the second spiral bodies 5. As illustrated in FIG. 4, the movement of the press member 15 towards the base 12 is stopped on top surfaces of the spacers 17, so that a thickness of the second spiral body 5 is determined by a thickness of the spacers 17.

Next, second shape-memory treatment is performed on the second spiral body 5 in STEP 5 of FIG. 1. The second shape-memory treatment is performed by, for example, storing the second spiral body 5, which is formed into a flat shape in a horizontal section, into a heating furnace, not illustrated, and holding a temperature of 150 to 900° C. for 3 to 120 minutes. Since the wire 2 is formed of the shape-memory alloy, as a result of performing the aforementioned operation, the shape that is flat in the horizontal section is stored into the second spiral body 5.

Figure 2:
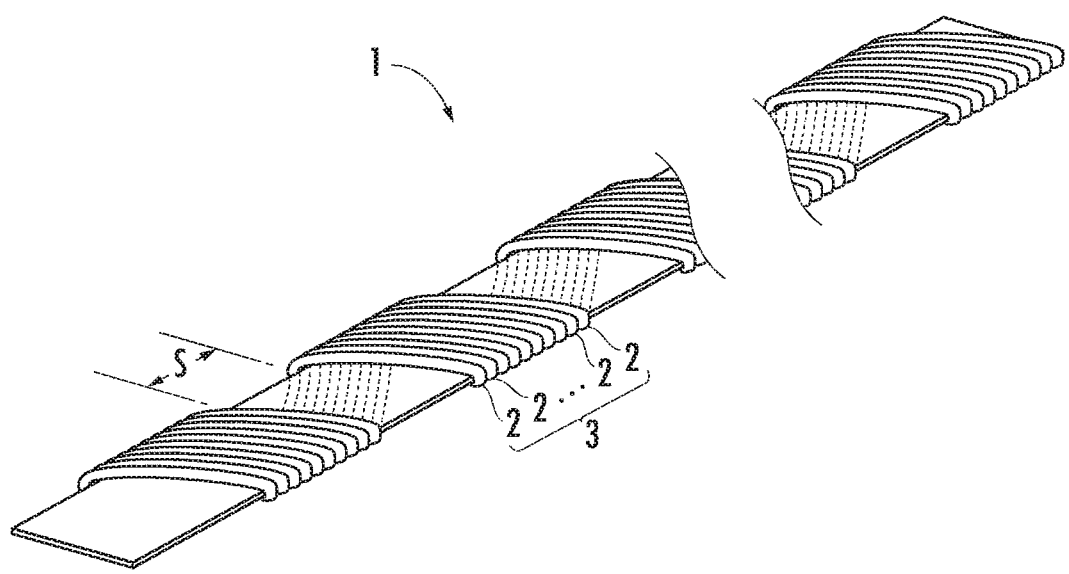
FIG. 2 is a plan view illustrating a method of forming a first spiral body.

Next, the winding core 4 is removed from the second spiral body 5 subjected to the second shape-memory treatment in STEP 6 of FIG. 2, thereby enabling to obtain the medical linear member of the present embodiment.

Figure 5A:
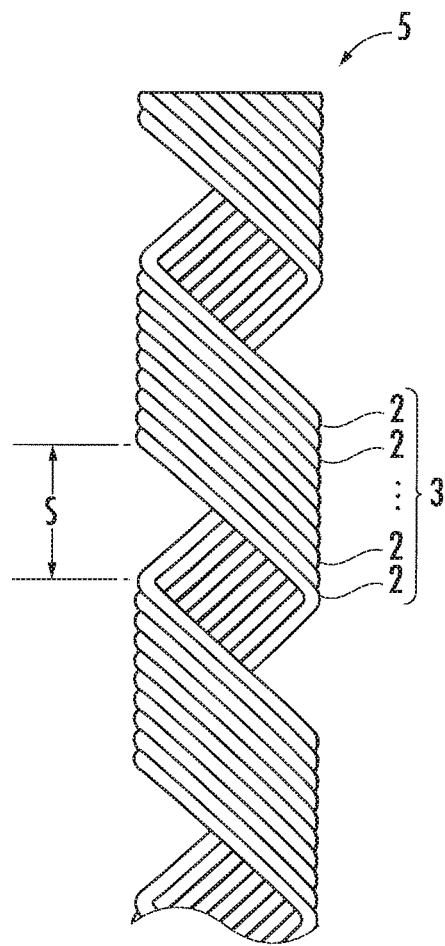
FIG. 5A is a plan view illustrating a configuration of a second spiral body and FIG. 5B is a sectional view taken along line VI-VI of FIG. 5A.
Figure 5B:
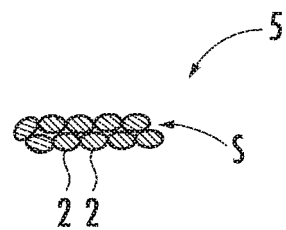

The second spiral body 5 as the medical linear member of the present embodiment is identical to the first spiral body 1 in a point that the base body 3 having the plurality of wires 2 arrayed in parallel to each other is spirally winded with the spaces S provided in the array direction, as illustrated in FIG. 5A. However, as illustrated in FIG. 5B, the second spiral body 5 is formed into the flat shape in the horizontal section, and no space is actually provided between the wires 2, 2 at a top and a bottom in the figure.

The medical linear member of the present embodiment may be the one which is obtained by further cutting the second spiral body 5 subjected to the second shape-memory treatment into a length of 30 to 50 mm.

Furthermore, it is described in the present embodiment that the spiral bodies 1 and 5 are formed of the base body 3 which is only single-layered. However, the spiral bodies 1 and 5 may be configured to have a plurality of base bodies 3 superposed with respect to axes thereof. Moreover, in such case, the base bodies 3, 3 superposed adjacently to each other may be spiraled in directions opposite to each other.

DESCRIPTION OF REFERENCE NUMERALS 1 first spiral body
2 wire
3 base body
4 winding core
5 second spiral body 11 compression jig
16 spring member

The invention claimed is:

1. A production method for a medical linear member, the production method comprising:
   a step of forming a first spiral body of an oval shape in a horizontal section by spirally winding a base body comprising an array of a plurality of wires formed of a shape-memory alloy, around a winding core formed of a flat plate with a space provided in an axial direction of the first spiral body between groups of windings of the plurality of wires;
   a step of subjecting the first spiral body to first shape-memory treatment by heating the first spiral body;
   a step of cutting the first spiral body into a first predetermined length;
   a step of forming a second spiral body of a flat shape in a horizontal section by compressing the first spiral body, which has been cut into the predetermined length, in a direction along a short diameter of the oval shape;
   a step of subjecting the second spiral body to second shape-memory treatment by heating the second spiral body; and
   a step of removing the winding core from the second spiral body subjected to the second shape-memory treatment.

2. The production method for the medical linear member according to claim 1, the production method further comprising a step of cutting the second spiral body subjected to the second shape-memory treatment into a second predetermined length.

3. The production method for the medical linear member according to claim 1, wherein the compression of the first spiral body is performed by arranging the first spiral body, which has been heated through the first shape-memory treatment, on a base in a state in which the first spiral body is kept heated and pressing a compression member from above.

4. The production method for the medical linear member according to claim 3, wherein the pressing of the compression member is performed by a spring member which biases the compression member in a direction towards the first spiral body.

* * * * *